US006528683B1

(12) United States Patent
Heidemann et al.

(10) Patent No.: US 6,528,683 B1
(45) Date of Patent: Mar. 4, 2003

(54) METHOD FOR PRODUCING SHELL CATALYSTS FOR THE CATALYTIC VAPOR-PHASE OXIDATION OF AROMATIC HYDROCARBONS AND CATALYSTS OBTAINED IN SUCH A MANNER

(75) Inventors: Thomas Heidemann, Weinheim (DE); Frank Rosowski, Mannheim (DE); Gerd Linden, Heidelberg (DE); Michael Seufert, Bad Dürkheim (DE); Gerhard Hefele, Römerberg (DE); Peter Michael Lorz, Wachenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/701,517

(22) PCT Filed: Jun. 9, 1999

(86) PCT No.: PCT/EP99/03828

§ 371 (c)(1),
(2), (4) Date: Nov. 30, 2000

(87) PCT Pub. No.: WO99/62637

PCT Pub. Date: Dec. 9, 1999

(30) Foreign Application Priority Data

Jun. 3, 1998 (DE) .......................................... 198 24 532

(51) Int. Cl.⁷ .......................... C07C 51/16; B01J 31/00; B32B 27/30
(52) U.S. Cl. ..................... 562/542; 562/412; 562/888; 502/104; 502/240; 428/522
(58) Field of Search ................................ 562/542, 412, 562/888; 502/104, 240, 242, 247; 428/522

(56) References Cited

U.S. PATENT DOCUMENTS

| 3,394,468 A | 7/1968 | Zeller et al. ..................... 34/57 |
| 3,565,829 A | 2/1971 | Friedrichsen et al. ........ 252/464 |
| 3,684,741 A | 8/1972 | Friedrichsen et al. ........ 252/435 |
| 3,799,886 A | 3/1974 | Felice et al. ................. 252/461 |
| 3,975,302 A | 8/1976 | Courty et al. ................ 252/455 |
| 4,036,783 A | 7/1977 | Blechschmitt et al. ...... 252/461 |
| 4,048,422 A | 9/1977 | Sackmann et al. ........... 526/203 |
| 4,234,712 A | 11/1980 | Keller et al. |
| 4,521,618 A | 6/1985 | Arntz et al. ................. 562/535 |
| 4,559,159 A | 12/1985 | Denzinger et al. .......... 252/174 |
| 4,990,589 A | 2/1991 | Towle et al. |
| 5,225,572 A * | 7/1993 | Hara et al. |
| 5,225,574 A | 7/1993 | Aichinger et al. ........... 549/248 |
| 5,227,446 A | 7/1993 | Denzinger et al. .......... 527/314 |
| 5,622,908 A | 4/1997 | Abel et al. .................. 502/339 |
| 5,792,719 A | 8/1998 | Eberle et al. ............... 502/178 |
| 6,071,994 A | 6/2000 | Hummerich et al. ........ 524/247 |

FOREIGN PATENT DOCUMENTS

| EP | 583 086 | 2/1994 |
| EP | 651 088 | 5/1995 |
| EP | 807 465 | 11/1997 |
| WO | WO 98/37967 | 9/1998 |

OTHER PUBLICATIONS

WO 98/00778, Sharagpani et al, USA, Jan. 8, 1998.*
Ullmann's Encyclopedia of Industrial Chemistry vol. A20 "Phthlaic Acid and Derivative" pp. 181–211.

* cited by examiner

Primary Examiner—J. Parsa
(74) Attorney, Agent, or Firm—Keil & Weinkauf

(57) ABSTRACT

The invention relates to a method for producing shell catalysts for the catalytic vapor-phase oxidation of aromatic carboxylic acids and/or carboxylic acid anhydrides comprised of a supporting core and of catalytically active metal oxides which are deposited in a shell-shaped manner on said supporting core. The inventive catalysts are obtained by spraying an aqueous active mass suspension, said suspension containing the active metal oxides, at higher temperatures onto the hot supporting material which has a temperature ranging from 50 to 450° C. The aqueous active mass suspension contains 1 to 10 wt. %, with regard to the solid content of the active mass suspension, a binding agent comprised of A) a polymerizate obtained by radical polymerization, containing 5 to 100 wt. % of monomers (a) in the form of ethylenically unsaturated acid anhydrides or ethylenically unsaturated dicarboxylic acids whose carboxyl groups can form an anhydride and containing 0 to 95 wt. % monoethylenically unsaturated monomers (b) with the provision that the monomers (a) and (b) comprise, on average, a maximum of 6 carbon atoms which are not functionalized with groups containing oxygen, and of B) an alkanolamine having at least 2 OH groups, a maximum of 2 nitrogen atoms and a maximum of 8 C-atoms, whereby the weight ratio A:B ranges from 1:0.05 to 1:1.

9 Claims, No Drawings

METHOD FOR PRODUCING SHELL CATALYSTS FOR THE CATALYTIC VAPOR-PHASE OXIDATION OF AROMATIC HYDROCARBONS AND CATALYSTS OBTAINED IN SUCH A MANNER

This application is a 371 of PCT/EP99/03828 claiming priority of Jun. 3, 1998.

Process for the preparation of coated catalysts for the catalytic gas-phase oxidation of aromatic hydrocarbons and catalysts obtainable in this way The invention relates to a process for the preparation of coated catalysts for the catalytic gas-phase oxidation of aromatic hydrocarbons to carboxylic acids and/or carboxylic anhydrides, to the carrier material of which is applied a layer of catalytically active metal oxides in layer form using certain binders, to catalysts obtainable in this way, and to a process for the catalytic gas-phase oxidation of aromatic hydrocarbons to carboxylic acids and/or carboxylic anhydrides with a gas comprising molecular oxygen in a fixed bed using these catalysts.

As is known, a large number of carboxylic acids and/or carboxylic anhydrides are prepared industrially by the catalytic gas-phase oxidation of aromatic hydrocarbons, such as benzene, the xylenes, naphthalene, toluene or durene, in fixed bed reactors, preferably tube bundle reactors. In this way, for example, benzoic acid, maleic anhydride, phthalic anhydride, isophthalic acid, terephthalic acid or pyromellithic [sic] anhydride are obtained. To do this, in general a mixture of a gas comprising molecular oxygen, for example air, and the starting material to be oxidized is passed through a plurality of tubes arranged in a reactor in which is located a packing of at least one catalyst. For temperature control, the tubes are surrounded by a heat exchanger medium, for example a salt melt. In spite of this thermostatting, the formation of so-called "hot spots" can occur in the catalyst packing, in which a higher temperature prevails than in the other part of the catalyst packing. These "hot spots" give rise to secondary reactions, such as the total combustion of the starting material or lead to the formation of undesirable secondary products which cannot be separated from the reaction product or can only be separated with great difficulty, for example to the formation of phthalide or benzoic acid, in the preparation of phthalic anhydride (PA) from o-xylene. In addition, the formation of a marked hot spot prevents rapid starting-up of the reactor since from a certain hot spot temperature the catalyst can be irreversibly damaged, so that the loading increase can only be carried out in small steps and has to be controlled very carefully.

For the reduction of this hot spot, a change was made in the art to arranging catalysts of differing activity in layers in the catalyst packing, where as a rule the less active catalyst is arranged in the fixed bed such that the reaction gas mixture comes into contact with it first, i.e. it is in the packing toward the gas inlet, whereas the more active catalyst is located toward the gas outlet of the catalyst packing. Thus either the catalysts of differing activity in the catalyst packing can be exposed to the reaction gas at the same temperature, or else the two layers of catalysts of differing activity can also be brought into contact with the reaction gas at different reaction temperatures under thermostatted conditions, as is described in DE-A 40 130 51.

Catalysts which have proven suitable are so-called coated catalysts, in which the catalytically active material is applied in layer form to a core of carrier material which is in general inert under the reaction conditions, such as quartz ($SiO_2$), porcelain, magnesium oxide, tin dioxide, silicon carbide, rutile, alumina ($Al_2O_3$), aluminum silicate, magnesium silicate (steatite), zirconium silicate or cerium silicate or mixtures of these carrier materials. In general, in addition to titanium dioxide in the form of its anatase modification, vanadium pentoxide serves as the catalytically active constituent of the catalytically active material of these coated catalysts. In addition, a multiplicity of other oxidic compounds, which as promoters affect the activity and selectivity of the catalyst, for example in that they decrease or increase its activity, can be contained in small amounts in the catalytically active material. As promoters of this type, mention may be made by way of example of the alkali metal oxides, in particular lithium, potassium, rubidium and cesium oxide, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide and phosphorus pentoxide. For example, the alkali metal oxides act as promoters which decrease the activity and increase the selectivity, whereas oxidic phosphorus compounds, in particular phosphorus pentoxide, increase the activity of the catalyst, but decrease its selectivity. These constituents are all known from the relevant technical literature.

For the preparation of coated catalysts of this type, for example, according to the process of DE-A 16 42 938 and DE-A 17 69 998 an aqueous solution or suspension, and/or solution or suspension comprising an organic solvent, of the active material constituents and/or of their precursor compounds, which in the following is referred to as a "mix", is sprayed onto the carrier material in a heated coating pan drum at elevated temperature until the desired active material content in the catalyst total weight is achieved. According to DE 21 06 796, the coating can also be carried out in fluidized bed coaters, such as are described, for example, in DE 12 80 756. On spraying in the coating pan drum and on coating in the fluidized bed, however, high losses occur, since considerable amounts of the mix are atomized or, due to abrasion, parts of the already stratified active material are abraded again and carried away by the off gas. Since the active material content in the total catalyst should in general have only a slight difference from the required value, as activity and selectivity of the catalyst are strongly affected by the amount of active material applied and the layer thickness of the shell, for the determination of the amount of active material applied, the catalyst in the outlined preparation procedure must be frequently colled, removed from the coating pan drum or the fluidized bed and reweighed. If too much active material has been deposited on the catalyst support, in general a subsequent, careful removal of the excessively high amount of active material applied is not possible without an adverse effect on the stability of the shell, in particular without crack formation in the catalyst shell.

In order to decrease these problems, a change was made in the art to adding organic binders, preferably copolymers, advantageously in the form of an aqueous dispersion, of vinyl acetate/vinyl laurate, vinyl acetate/acrylate, vinyl acetate/maleate and vinyl acetate/ethylene to the mix, according to EP-A 07 442 14 amounts of binder of 10–20% by weight, based on the solids content of the mix, being employed. If the mix is applied to the support without organic binders, coating temperatures of over 150° C. are advantageous. In the case of addition of the binders indicated, according to DE 210 67 96 the coating temperatures utilizable, at 70–130° C., are markedly lower. The binders applied burn off within a short time after the filling of the catalyst and putting into operation of the reactor. The addition of binder moreover has the advantage that the active material adheres well to the support, so that transport and filling of the catalyst are facilitated.

During the combustion, however, a loosening of the adhesion of the active material layer on the support occurs. This is normally not critical, since the catalyst in the reactor tube is no longer exposed to strong mechanical stresses. In particular in the case of relatively large amounts of binder additive, however, it cannot be ruled out that the active material layer is loosened so much that it is slowly removed under reaction conditions by the gas mixture flowing through. This has the result that the long-term stability of the catalyst is reduced and the salt bath temperature of the reactor to be set for the required PA quality has to be steadily increased, which in turn has an adverse effect on the PA yield achievable. In addition, on combustion of the binder additive, in addition to odor nuisance and further adverse environmental compatibility effects due to ignition of decomposition products of the binder additive, detonations can occur which can endanger the safe operation of the reactor. Finally, it is useful for reasons of cost to minimize the amount necessary for the desired effect of the binder additive [sic].

It is thus the object of the present invention to find a process for the preparation of coated catalysts for the catalytic gas-phase oxidation of aromatic hydrocarbons to carboxylic acids and/or carboxylic anhydrides which, while retaining the advantages which can be achieved by the addition of binder, avoids the outlined disadvantages of binder addition.

We have found that this object is achieved by addition of a specific organic binder, which surprisingly leads to the abovementioned desired advantages even in additions of <10% by weight, based on the solids content of the mix. In detail, the object was achieved according to the invention by a process for the preparation of coated catalysts for the catalytic gas-phase oxidation of aromatic carboxylic acids and/or carboxylic anhydrides, consisting of a carrier core and catalytically active metal oxides applied thereto in layer form, obtained by spraying an aqueous active material suspension comprising the active metal oxides at relatively high temperatures onto the carrier material at 50 to 450° C., wherein the aqueous active material suspension contains 1 to 10% by weight, based on the solids content of the active material suspension, of a binder, consisting of A) a polymer obtained by free-radical polymerization, comprising 5 to 100% by weight of monomers (a) in the form of ethylenically unsaturated acid anhydrides or ethylenically unsaturated dicarboxylic acids whose carboxyl groups can form an anhydride and 0 to 95% by weight of further monoethylenically unsaturated monomers (b), with the proviso that the monomers (a) and (b) on average have at most 5, preferably 2 to 4, carbon atoms which are not functionalized by groups comprising oxygen, and B) an alkanolamine having at least 2 OH groups, at most 2 nitrogen atoms, preferably a nitrogen atom and at most 8 C atoms, the weight ratio A:B being 1:0.05 to 1:1.

The alkanolamine here has the function of an agent acting as a crosslinking via the formation of ester groups. This "curing" occurs on spraying the "mix" onto the support at elevated temperature.

The binders to be used according to the invention should contain as few carbon atoms as possible in the chain, i.e. as few groups as possible not comprising oxygen, such as C atoms which are not functionalized by OH, COOH or COOR groups, in order to keep the evolution of heat low during later combustion of the binder in the reactor and to avoid damage by overheating the catalyst. These conditions is [sic] expressed by the characterization of the total carbon number of the monomers indicated above.

According to another definition, which characterizes the same situation, the atomic ratio C:O in the binder is at most 3:1, preferably up to 2.5:1 and particularly preferably up to 2:1.

In detail, suitable binders for the process according to the invention are those described in WO 97/31036, which fulfill the abovementioned conditions. With respect to the selection criteria indicated, reference is therefore expressly made to WO 97/31036 on the details with respect to the binder.

Accordingly, maleic acid, maleic anhydride, itaconic acid, 1,2,3,6-tetrahydrophthalic acid, 1,2,3,6-tetrahydrophthalic anhydride, the alkali metal and ammonium salts or mixtures thereof are preferably employed as monomers (a), Maleic acid and maleic anhydride are particularly preferred.

Monomers (b) which can be employed are, for example:

monoethylenically unsaturated $C_3$- to $C_6$-monocarboxylic acids, such as, for example, acrylic acid, methacrylic acid, ethylacrylic acid, allylacetic acid, crotonic acid, vinylacetic acid, maleic acid monoesters such as monomethyl maleate, their mixtures or their alkali metal and ammonium salts, and further vinyl and allyl alkyl ethers, it being possible for the alkyl radical to carry other substituents such as a hydroxyl group, or one or more alkoxylate groups, such as, for example, methyl vinyl ether, ethyl vinyl ether, propyl vinyl ether, isobutyl vinyl ether, vinyl-4-hydroxybutyl ether, and the corresponding allyl ethers or their mixtures, arcylamides [sic] and alkyl-substituted acrylamides, such as, for example, acrylamide, methacrylamide, N-tert-butylacrylamide, methyl(meth)acrylamide, sulfo group-containing monomers, such as, for example, allylsulfonic acid, methallylsulfonic acid, styrenesulfonate, vinylsulfonic acid, allyloxybenzene-sulfonic acid, 2-acrylamido-2-methylpropanesulfonic acid, their corresponding alkali metal or ammonium salts or their mixtures, $C_1$- to $C_4$-alkyl esters or $C_1$- to $C_4$-hydroxyalkyl esters of acrylic acid, methacrylic acid or maleic acid or esters of $C_1$- to $C_4$-alcohols, alkoxylated with 2 to 50 mol of ethylene oxide, propylene oxide, butylene oxide or mixtures thereof, with acrylic acid, methacrylic acid or maleic acid (monomer $b_6$), such as, for example, methyl (meth)acrylate or ethyl (meth)acrylate, vinyl and allyl esters of $C_1$- to $C_4$-monocarboxylic acids such as, for example, vinyl formate, vinyl acetate, vinyl propionate or vinyl butyrate. Further monomers which may additionally be mentioned are: alkyl alcohol, acrolein, methacrolein or mixtures thereof.

Preferred monomers (b) are acrylic acid, methacrylic acid, methyl vinyl ether, ethyl vinyl ether, vinyl acetate or mixtures thereof.

Acrylic acid, methacrylic acid and mixtures thereof are particularly preferred.

The polymerizate preferably contains 20 to 90% by weight, in particular 50 to 80% by weight, of the monomers (b).

The polymers of the monomers (a) and, if appropriate, (b) can be prepared by customary polymerization processes, e.g.

by substance, emulsion, suspension, dispersion, precipitation and solution polymerization. The polymerization processes mentioned are preferably carried out with exclusion of oxygen, preferably in a stream of nitrogen. The customary equipment is used for all polymerization methods, e.g. stirring vessels, stirring vessel cascades, autoclaves, tubular reactors and kneaders. The polymerization is preferably carried out by the solution, emulsion, precipitation or suspension polymerization method. The solution and emulsion polymerization methods are particularly preferred. The polymerization can be carried out in solvents or diluents, such as, for example, toluene, o-xylene, p-xylene, cumene, chlorobenzene, ethylbenzene, technical mixtures of alkylaromatics, cyclohexane, technical aliphatic mixtures, acetone, cyclohexanone, tetrahydrofuran, dioxane, glycols and glycol derivatives, polyalkylene glycols and their derivatives, diethyl ether, tert-butyl methyl ether, methyl acetate, isopropanol, ethanol, water or mixtures such as, for example, isopropanol/water mixtures. The solvent or diluent preferably used is water, optionally with amounts of up to 60% by weight of alcohols or glycols. Water is particularly preferably employed.

The polymerization can be carried out at temperatures from 20 to 300° C., preferably from 60 to 200° C. Depending on the choice of polymerization conditions, weight-average molecular weights, e.g. from 800 to 5,000,000, in particular from 1000 to 1,000,000, can be set. Preferably, the weight-average molecular weights $M_w$ are above 15,000. Weight-average molecular weights of 15,000 to 600,000 are particularly preferred. $M_w$ is determined by gel-permeation chromatography.

The polymerization is preferably carried out in the presence of compounds forming free radicals. Up to 30% by weight, preferably 0.05 to 15% by weight, particularly preferably 0.2 to 8% by weight, based on the monomers employed in the polymerization, of these compounds is needed. In the case of multicomponent initiator systems (e.g. redox initiator systems), the above weight data relate to the sum of the components.

Suitable polymerization initiators are, for example, peroxides, hydroperoxides, peroxydisulfates, percarbonates, peroxyesters, hydrogen peroxide and azo compounds. Examples of initiators which can be water-soluble or alternatively water-insoluble are hydrogen peroxide, dibenzoyl peroxide, dicyclohexyl peroxydicarbonate, dilauroyl peroxide, methyl ethyl ketone peroxide, di-tert-butyl peroxide, acetylacetone peroxide, tert-butyl hydroperoxide, cumene hydroperoxide, tert-butyl perneodecanoate, tert-amyl perpivalate, tert-butyl perpivalate, tert-butyl perneohexanoate, tert-butyl per-2-ethylhexanoate, tert-butyl perbenzoate, lithium, sodium, potassium and ammonium peroxydisulfate, azodiisobutyronitrile, 2,2'-azobis(2-amidinopropane) dihydrochloride, 2-(carbamoylazo) isobutyronitrile and 4,4-azobis(4-cyanovaleric acid).

The initiators can be used on their own or as a mixture with one another, e.g. mixtures of hydrogen peroxide and sodium peroxydisulfate. For polymerization in aqueous medium, water-soluble initiators are preferably employed.

The known redox initiator systems can also be used as polymerization initiators. Such redox initiator systems contain at least one peroxide-containing compound in combination with a redox coinitiator, e.g. sulfur compounds having a reducing action, for example bisulfites, sulfites, thiosulfates, dithionites and tetrathionates of alkali metals and ammonium compounds. Thus combinations of peroxodisulfates with alkali metal or ammonium hydrogensulfites can be employed, e.g. ammonium peroxydisulfate and ammonium disulfite. The amount of the peroxide-containing-compound relative to the redox coinitiator is 30:1 to 0.05:1.

In combination with the initiators or the redox initiator systems, transition metal catalysts can additionally be employed, e.g. salts of iron, cobalt, nickel, copper, vanadium and manganese. Suitable salt [sic] are, for example, iron (II) sulfate, cobalt (II) chloride, nickel (II) sulfate, copper (I) chloride. Based on monomers, the transition metal salt having a reducing action is employed in a concentration from 0.1 ppm to 1000 ppm. Thus combinations of hydrogen peroxide with iron(II) salts can be employed, such as, for example, 0.5 to 30% hydrogen peroxide and 0.1 to 500 ppm Mohr's salt.

In combination with the abovementioned initiators, it is also possible in the case of polymerization in organic solvents to additionally use redox coinitiators and/or transition metal catalysts, e.g. benzoin, dimethylaniline, ascorbic acid and soluble organic complexes of heavy metals, such as copper, cobalt, iron, manganese, nickel and chromium. The amounts of redox coinitiators and transition metal catalysts customarily used here are customary approximately 0.1 to 1000 ppm, based on the amounts of monomers employed.

If polymerization of the reaction mixture is started at the lower limit of the temperature range suitable for the polymerization and then completed at a higher temperature, it is expedient to use at least two different initiators which decompose at differing temperatures, such that an adequate concentration of free radicals is available in each temperature range.

In order to prepare polymers having a low average molecular weight, it is often expedient to carry out the copolymerization in the presence-of regulators. Customary regulators can be used for this purpose, such as, for example, compounds containing organic SH groups, such as 2-mercaptoethanol, 2-mercaptopropanol, mercaptoacetic acid, tert-butylmercaptan, n-octylmercaptan, n-dodecylmercaptan and tert-dodecylmercaptan, $C_1$- to $C_4$-aldehydes, such as formaldehyde, acetaldehyde, propionaldehyde, hydroxylammonium salts such as hydroxylammonium sulfate, formic acid, sodium bisulfite or isopropanol. The polymerization regulators are in general employed in amounts from 0.1 to 10% by weight, based on the monomers. The choice of the suitable solvent can also bring an influence to bear on the average molecular eight. Thus polymerization in the presence of diluents having benzylic H atoms leads to a lowering of the average molecular eight as a result of chain transfer.

If the polymerization is carried out by the method of emulsion, precipitation, suspension or dispersion polymerization, it can be advantageous to stabilize the polymer droplets or polymer particles by means of surface-active auxiliaries. Typically, emulsifiers or protective colloids are used to this end. Anionic, nonionic, cationic and amphoteric emulsifiers are suitable. Anionic emulsifiers are, for example, alkylbenzenesulfonic acids, sulfonated fatty acids, sulfosuccinates, fatty alcohol sulfates, alkylphenol sulfates and fatty alcohol ether sulfates. Nonionic emulsifiers which can be used are, for example, alkylphenol ethoxylates, primary alcohol ethoxylates, fatty acid ethoxylates, alkanolamide ethoxylates, fatty amine ethoxylates, EO/PO block copolymers and alkylpolyglucosides. Cationic and amphoteric emulsifiers which can be used are, for example: quaternized amine alkoxylates, alkylbetaines, alkylamidobetaines and sulfobetaines.

Typical protective colloids are, for example, cellulose derivatives, polyethylene glycol, polypropylene glycol, copolymers of ethylene glycol and propylene glycol, polyvinyl acetate, polyvinyl alcohol, polyvinyl ether, starch and starch derivatives, dextran, polyvinylpyrrolidone, polyvinylpyridine, polyethyleneimine, polyvinylimidazole, polyvinylsuccinimide, polyvinyl-2-methylsuccinimide, polyvinyl-1,3-oxazolid-2-one, polyvinyl-2-methylimidazoline and copolymers containing maleic acid or maleic anhydride, such as are described, for example, in DE 2 501 123.

The emulsifiers or protective colloids are customarily employed in concentrations from 0.05 to 20% by weight, based on the monomers.

If polymerization is carried out in aqueous solution or dilution, the monomers can be completely or partly neutralized by bases before or during the polymerization. Suitable bases are preferably nitrogen-free bases, for example alkali metal or alkaline earth metal compounds such as sodium hydroxide, potassium hydroxide, calcium hydroxide, magnesium oxide and sodium carbonate.

Particularly preferably, the ethylenically unsaturated carboxylic acids are not neutralized before and during the polymerization. Preferably, no neutralizing agent, apart from alkanolamine (B), is added even after the polymerization. The polymerization can be carried out continuously-or batchwise by a large number of variants. Customarily, part of the monomers is optionally introduced into a suitable diluent or solvent and, if appropriate, in the presence of an emulsifier, a protective colloid or further auxiliaries, inertized and the temperature is increased until the desired polymerization temperature has been achieved. However, only a suitable diluent can also be introduced. Within a defined period, the free-radical initiator, further monomers and other auxiliaries, such as, for example, regulators or crosslinkers, are in each case optionally metered into a diluent. Different lengths of the addition time can be selected. For example, a longer addition time can be selected for initiator addition than for monomer addition.

If the polymer is obtained according to the solution polymerization process, customarily no removal of the solvent is necessary. Nevertheless, if it is wished to isolate the polymer, spray drying, for example, can be carried out.

If the polymer is prepared by a solution, precipitation or suspension polymerization method in a steam-volatile solvent or solvent mixture, the solvent can be removed by passing in steam so as to obtain an aqueous solution or dispersion. The polymer can also be removed from the organic diluent by means of a drying process.

Preferably, the polymers (A) are present in the form of an aqueous dispersion or solution having solids contents of preferably 10 to 80% by weight, in particular 40 to 65% by weight.

Polymer (A) can also be obtained by grafting maleic acid or maleic anhydride or a monomer mixture containing maleic acid or maleic anhydride onto a graft base. Suitable graft bases are, for example, monosaccharides, oligosaccharides, modified polysaccharides and alkyl polyglycol ethers. Such graft polymers are described, for example, in DE 4 003 172 and EP 116 930.

As component B) alkanolamines having at least two OH groups and at most two nitrogen atoms, preferably having one nitrogen atom, are employed. Preferred alkanolamines are those of the formula

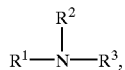

I in which $R^1$ is an H atom, a $C_1$–$C_4$-alkyl group or a $C_1$–$C_4$-hydroxyalkyl group and $R^2$ and $R^3$ are a $C_1$–$C_4$-hydroxyalkyl group.

Particularly preferably $R^2$ and $R^3$ independently of one another are a $C_2$–$C_4$-hydroxyalkyl group and $R^1$ is an H atom, a $C_1$–$C_3$-alkyl group or a $C_2$–$C_4$-hydroxyalkyl group.

Compounds of the formula I which may be mentioned are, for example, diethanolamine, triethanolamine, diisopropanolamine, triisopropanolamine, methyldiethanolamine, butyldiethanolamine and methyldiisopropanolamine. Triethanolamine is particularly preferred.

For the preparation of the binders to be used according to the invention, the polymer (A) and the alkanolamine (B) are preferably employed in such a ratio to one another that the molar ratio of carboxyl groups of component (A) and the hydroxyl groups of component (B) is 20:1 to 1:1, preferably 8:1 to 5:1 and particularly preferably 5:1 to 1.7:1 (the anhydride groups are in this case calculated as 2 carboxyl groups).

The binders are prepared here, for example, simply by adding the alkanolamine to the aqueous dispersion or solution of the polymers (A).

The binders to be used according to the invention preferably contain less than 1.0% by weight, particularly preferably less than 0.5% by weight and very particularly preferably less than 0.3% by weight, in particular less than 0.1% by weight, based on the sum of (A)+(B), of a phosphorus-containing reaction accelerator. Phosphorus-containing reaction accelerators are mentioned in EP-A 651 088 and EP-A 583 086. These are, in particular, alkali metal hypophoshpites [sic], phosphites, polyphosphates, dihydrogenphosphates, polyphosphoric acid, hypophosphoric acid, phosphoric acid, alkylphosphinic acid or oligomers or polymers of these salts and acids.

The binders, however, preferably do not contain any phosphorus-containing reaction accelerators or any amounts of phosphorus-containing compound effective for accelerating the reaction. The binders can contain an esterification catalyst, such as, for example, sulfuric acid or p-toluenesulfonic acid. As a rule, the binders to be used according to the invention are used as the only binders for the preparation of the coated catalysts. However, they can also be used together with other binders.

The catalysts prepared by this process with addition of the binder to be used according to the invention in principle are none other than those described in the patent specifications mentioned at the outset, to which reference is hereby made. As a rule, these are so-called coated catalysts, in which the catalytically active material is applied in layer form to a carrier material which is in general inert under the reaction conditions, such as quartz ($SiO_2$), porcelain, magnesium oxide, tin dioxide, silicon carbide, rutile, alumina ($Al_2O_3$), aluminum silicate, magnesium silicate (steatite), zirconium silicate or cerium silicate or mixtures of these carrier materials. In general, in addition to titanium dioxide in the form of its anatase modification, vanadium pentoxide serves as the catalytically active constituent of the catalytically active material of these coated catalysts. In addition, a multiplicity of other oxidic compounds, which as promoters affect the activity and selectivity of the catalyst, for example in that they decrease or increase its activity, can be contained in small amounts in the catalytically active material. As promoters of this type, mention may be made by way of example of the alkali metal oxides, in particular lithium, potassium, rubidium and cesium oxide, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide and phosphorus pentoxide. For example, the alkali metal oxides act as promoters which decrease the activity and increase the selectivity, whereas oxidic phosphorus compounds, in particular phosphorus pentoxide, increase the activity of the catalyst, but decrease its selectivity.

The catalysts are prepared by applying the active material to the support in a manner known per se by spraying an active material mix onto a carrier preheated to 50–450° C., e.g. in a coating pan drum or in fluidized bed coaters as is described, for example, in DE 21 06 796, DE 17 69 998, DE 16 42 938 or DE 25 10 994. Before the start of spraying, the binder is added to the mix. Preferably, coating is carried out in the temperature range 100 to 250° C. and particularly preferably at 140 to 200° C., since in these temperature ranges optimum curing of the binder additive takes place.

This curing process during the coating results in even small additions of 1 to 10% by weight, preferably 4 to 8% by weight, of binder, based on the solids content of the mix, being sufficient in order to markedly increase the adhesion of the active material to the support and to bring about a marked decrease in the mix losses during the coating process. An increase in the binder additive to above 10% by weight does additionally lead to a further slight direct improvement in the adhesion; these relatively large amounts of binder additive, however, also lead to the adhesion of the active material after calcination of the catalyst at 400° C. being greatly decreased, while catalysts having binder additives of less than 10% by weight still have good abrasion vales even after calcination.

In addition, neither odor nuisances nor further adverse environmental compatibility effects are to be found on combustion of the small amounts required of the novel binder additive after the filling of the catalyst and putting into operation of the reactor. Ignition of decomposition products of the binder additive, which can lead to detonations and thus endanger the safe operation of the reactor, are likewise not observed.

The carboxylic acids and carboxylic anhydrides, in particular phthalic anhydride, are prepared in a manner known per se by catalytic gas-phase oxidation of aromatic hydrocarbons, in particular o-xylene, using the catalysts prepared according to the invention, as is shown by way of summary in K. Towae, W. Enke, R. Jäckh, N. Bhargawa "Phthalic Acid and Derivatives" in Ullmann's Encyclopedia of Industrial Chemistry Vol. A 20, 1992, p. 181. In this case, 2 or more catalyst layers are preferably applied, of which preferably only one layer is charged on the gas inlet side with the catalysts according to the invention, since the catalyst loading is lower on the gas outlet side and a standard catalyst is therefore sufficient. In detail, for example, when using the novel catalysts a procedure is used in which the catalysts are first filled into the reaction tubes of the reactor, which are thermostatted to the reaction temperature from the outside, for example by means of salt melts. The reaction gas is passed over the catalyst packing prepared in this way at temperatures from in general 300 to 450° C., preferably 320 to 420° C. and particularly preferably from 340 to 400° C. and at an overpressure of in general 0.1 to 2.5 bar, preferably from 0.3 to 1.5 bar, at a space velocity of in general 750 to 5000 h$^{-1}$.

The reaction gas fed to the catalyst is in general produced by mixing of a gas containing molecular oxygen, which apart from oxygen can additionally contain suitable reaction moderators and/or diluents, such as steam, carbon dioxide and/or nitrogen, with the aromatic hydrocarbon to be oxidized, where the gas containing molecular oxygen in general can contain 1 to 100 mol %, preferably 2 to 50 mol % and particularly preferably 10 to 30 mol % of oxygen, 0 to 30 mol %, preferably 0 to 10 mol % of hydrogen as well as 0 to 50 mol %, preferably 0 to 1 mol %, of carbon dioxide, remainder nitrogen. For production of the reaction gas, the gas containing molecular oxygen is in general charged with 30 g to 150 g per Nm$^3$ of gas of the aromatic hydrocarbon to be oxidized.

EXAMPLE 1

Preparation of Standard Catalyst I without Binder Addition (Comparison Example)

50.0 kg of steatite (magnesium silicate) rings having an external diameter of 8 mm, a length of 6 mm and a wall thickness of 1.5 mm were heated to 160° C. in a coating pan drum and sprayed with a suspension of 25.0 kg of anatase (analysis: 0.18% S; 0.08% P; 0.24% Nb; 0.01 [sic] Na; 0.01 [sic] K; 0.004% Zr; 0.004% Pb) of a BET surface area of 20 m$^2$/g, 1.81 kg of vanadyl oxalate, 0.143 kg of cesium sulfate, 38 kg of water and 9.85 kg of formamide until the weight of the layer applied in this manner was 10.0% of the total weight (after calcination at 450° C.) of the finished coated catalyst. The catalytically active material applied in this manner, i.e. the catalyst shell, consisted of 0.40% by weight of cesium (calculated as Cs), 4.0% by weight of vanadium (calculated as $V_2O_5$) and 95.6% by weight of titanium dioxide. For coating, 17.8 g of mix were needed, i.e. about 12% of the sprayed mix are lost by discharge during application. The abrasion according to the triple fall test* was 14.4%, after calcination at 400° C. the abrasion was 23.7%.

*Fall test: about 50 G [sic] of catalyst are allowed to fall through a 3 m long tube of 25 mm internal diameter. The catalyst falls into a dish standing under the tube, is separated from the dust formed on impact and is again allowed to fall through the tube. The total mass loss after the triple fall test with respect to the amount of active material applied (=100%) is a measure of the abrasion resistance of the catalyst. In the fall test after calcination, the procedure is as above, after 50 g of catalyst have been heated at 400° C. for 1 h.

EXAMPLE 2 a) Preparation of the binder (according to WO 97/31036)

A copolymer of acrylic acid/maleic acid in weight ratio 75:25 is polymerized at 110° C. using hydrogen peroxide as a free-radical initiator according to the details of EP-A 75 820. The solids content of the polymer solution obtained is 44.6%, the pH 0.7 and the $M_w$: 90,000. 882.0 g of polymer-containing polymer solution are mixed with 118.0 g of triethanolamine. The binder thus obtained has a solids content of 49.4% by weight, a pH of 2.9 and a viscosity of 3700 mPas.

b) Preparation of the Catalysts A-C according to the Invention with Binder Addition The procedure is as indicated under Example 1 with the proviso that 17.0 kg of mix in each case were treated with 400 g, 800 g or 1050 g of the aqueous binder according to (a) before spraying onto the catalyst. The steati [sic] rings were sprayed with the mix modified in this way until the weight of the layer applied in this manner was 10.0% of the total weight (after calcination at 450° C.) of the finished coated catalyst. Required mix amounts, mix loss and abrasion values are listed in Table 1 below.

TABLE 1

| Catalyst | 49.4% strength binder solution | Mix consumption | Mix loss | Binder content of the active materials | Abrasion 1 | Abrasion 2 |
|---|---|---|---|---|---|---|
| A | 400 g | 16.2 kg | 2% | 3.6% | 8.2% | 11.4% |
| B | 800 g | 16.5 kg | 4% | 7.2% | 3.2% | 12.9% |
| C | 1050 g | 16.3 kg | 3% | 9.5% | 2.3% | 20.1% |

Abrasion 1: Fall test with original sample;
Abrasion 2: Fall test 40 with calcined sample (400° C.)

Combustion of the Binder Additive

To check whether substances which are an odor nuisance or have an adverse environmental effect are released during combustion of the binder additive, catalyst C was heated from 30° C. to 610° C. [sic] with passage of air (temperature increase: 5° C./min); the mass decrease as well as the resulting gaseous (decomposition) products were analyzed on-line with the aid of coupled differential thermogravimetry/FTIR spectroscopy. It was found that all volatile constituents up to 400° C. are removed; in addition, only $H_2O$, $CO$ and $CO_2$ are detectable in the gas phase. It was not possible to identify any decomposition products which were an odor nuisance, had an adverse effect on the environment or were flammable.

EXAMPLE 3

Preparation of a Standard Catalyst II Without Binder Addition 50 kg of steatite (magnesium silicate) rings having an external diameter of 8 mm, a length of 6 mm and a wall thickness of 1.5 mm were heated to 160° C. in a coating pan drum and sprayed with a suspension of 28.6 kg of anatase having a BET surface area of 20 $m^2/g$, 4.11 kg of vanadyl oxalate, 1.03 kg of antimony trioxide, 0.179 kg of ammonium hydrogenphosphate, 0.046 kg of cesium sulfate, 44.1 kg of water and 9.14 kg of formamide until the weight of the layer applied was 10.5% of the total weight of the finished catalyst (after calcination at 450° C. [sic]). The catalytically active material applied in this manner, i.e. the catalyst shell, consisted of 0.15% by weight of phosphorus (calculated as P), 7.5% by weight of vanadium (calculated as $V_2O_5$), 3.3% by weight of antimony (calculated as $Sb_2O_3$), 0.1% by weight of cesium (calculated as Cs) and 89.05% by weight of titanium dioxide. For coating, 17.2 kg of mix were needed, i.e. about 6% of the sprayed mix were lost by discharge on application. The abrasion according to the triple fall test was 8.0%.

EXAMPLE 4

Preparation of the Catalyst D According to the Invention and a Comparison Catalyst E Having over 10% Binder Addition The procedure was as indicated in Example 3, with the proviso that 17.0 kg of mix in each case were treated with 700 g or 1500 g of the aqueous binders according to Example 2a before spraying onto the catalyst. The steati [sic] rings were sprayed with the mix modified in this way until the weight of the layer applied in this manner was 10.5% of the total weight (after calcination at 450° C.) of the finished coated catalyst. Required mix amounts, Mix loss and abrasion values are listed in Table 2 below.

TABLE 2

| Catalyst | Binder solution | Mix consumption | Mix loss | Binder content of the active material | Abrasion 1 | Abrasion 2 |
|---|---|---|---|---|---|---|
| D | 700 g | 16.4 kg | 2% | 6.3% | 5.2% | 19.6% |
| E | 1500 g | 16.3 kg | 1% | 13.4% | 3.3% | 51.3% |

Abrasion 1: Fall test with original sample;
Abrasion 2: Fall test with calcined sample (400° C.)

EXAMPLE 5

Preparation of Phthalic Anhydride

From the bottom upwards, 1.30 m of the catalyst II and then 1.60 m of the catalysts I (comparison) or C (inventive) in each case were filled into a 3.85 m long iron tube having an internal diameter of 25 mm. The iron tube was surrounded by a salt melt for temperature regulation. 4.0 $Nm^3$ of air with loadings of 98.5% strength by weight o-xylene of 40 to approximately 80 $g/Nm^3$ of air were passed through the tube hourly from the top downwards. In this process, at 75–85 g loading, the results summarized in Table 3 below were obtained (yield denotes the phthalic anhydride (PA) obtained in percent by weight, based on 100% strength o-xylene; raising time denotes the days required for the loading increase from 40 to 80 $g/Nm^3$).

TABLE 3

| Example catalyst combination | Salt bath temperature (° C.) | Average PA yield (% by weight) | Raising time (d) |
|---|---|---|---|
| I/II (Comparison) | 352 | 113.3 | 36 |
| C/II | 354 | 113.5 | 25 |

EXAMPLES 6–15

Essentially identical results with respect to Abrasion 1, Abrasion 2, PA yield and raising time are obtained if the binders of Table 4 below are used for catalyst preparation.

TABLE 4

| | Polymer A | | | | | | Binder from A + B | | |
|---|---|---|---|---|---|---|---|---|---|
| Example | Monomer a Type/(%) | Monomer b Type/(%) | Solids content (%) | pH | $M_w$ | Polymer A (g) | Monomer B Type/(g) | Solids content (%) | pH | Viscosity (mPas) |
| 6 | MA/60 | AA/60 | 40.3 | 1.3 | 125000 | 810 | TEA/190 | 46.3 | 2.9 | 1000 |
| 7 | MA/25 | MAA/75 | 42.7 | 0.9 | 90000 | 913 | TEA/87 | 48.5 | 3.4 | 3500 |
| 8 | MA/20 | MVE/80 | 41.5 | 1.5 | 75000 | 788 | TEA/212 | 46.5 | 3.7 | 14000 |

TABLE 4-continued

| | Polymer A | | | | | | Binder from A + B | | |
|---|---|---|---|---|---|---|---|---|---|
| Example | Monomer a Type/(%) | Monomer b Type/(%) | Solids content (%) | pH | $M_w$ | Polymer A (g) | Monomer B Type/(g) | Solids content (%) | pH | Viscosity (mPas) |
| 9 | MA/20 | AA/80 | 43.3 | 0.8 | 150000 | 825 | MDA/175 | 47.3 | 3.4 | 7000 |
| 10 | MA/40 | AA/60 | 40.7 | 1.2 | 60000 | 899 | MDA/101 | 45.3 | 3.1 | 950 |
| 11 | MAN/30 | AA/70 | 42.8 | 1.9 | 200000 | 773 | TEA/227 | 48.5 | 2.9 | 2600 |
| 12 | MAN/20 | MAA/80 | 43.6 | 1.4 | 80000 | 812 | TEA/188 | 48.9 | 3.4 | 4900 |
| 13 | MAN/20 | MVE/80 | 41.9 | 0.7 | 60000 | 900 | TEA/100 | 46.8 | 3.6 | 11200 |
| 14 | THP/30 | AA/70 | 44.0 | 1.0 | 25000 | 801 | TEA/199 | 50.1 | 3.2 | 2500 |
| 15 | THP/40 | AA/60 | 42.0 | 1.9 | 20000 | 875 | MDA/125 | 47.1 | 2.8 | 6700 |

MA Maleic acid
MAN Maleic anhydride
THP 1,2,3,6-Tetrahydrophthalic acid
AA Acrylic acid
MAA Methacrylic acid
MVE Methyl vinyl ether
TEA Triethanolamine
MDA Methyldiethanolamine
$M_w$ weight-average molecular weight

We claim:

1. A process for the preparation of coated catalysts for the catalytic gas phase oxidation of aromatic hydrocarbons to a member selected from carboxylic acids and anhydrides, said catalysts consisting essentially of a carrier core and catalytically active metal oxides applied thereto in layer form, which process comprises spraying an aqueous active material suspension containing the active metal oxides at relatively high temperatures onto the carrier core material at 50 to 450° C., wherein the aqueous active material suspension contains 1 to 10% by weight, based on solids content of the active material suspension, of a binder, consisting essentially of
   A) a polymer obtained by free-radical polymerization comprising 5 to 100% by weight of monomers (a) in the form ethylenically unsaturated acid anhydrides or ethylenically unsaturated dicarboxylic acids whose carboxyl groups can form an anhydrides and 0 to 95% by weight of further monoethylenically unsaturated monomers(b), with the proviso that the monomers (a) and (b) on average have at most 5 carbon atoms which are not functionalized by groups comprising oxygen, and
   B) an alkanolamine having at least 2 OH groups, at most 2 nitrogen atoms and at most 8 C-atoms, the weight ratio A:B being 1:0.05 to 1:1.

2. A process as claimed in claim 1, wherein the monomers (a) and (b) have 2 to 4 C atoms and the alkanolamines have a nitrogen atom.

3. A process as claimed in claim 1, wherein, in the binder formed from (A) and (B), the atomic ratio C:O is at most 3:1.

4. A process as claimed in claim 1, wherein the temperature of the carrier material to be coated is 100–250° C.

5. A process as claimed in claim 1, wherein the temperature of the carrier material to be coated is 140–200° C.

6. A process as claimed in claim 1, wherein the organic constituents of the binder additive are 4–8% by weight, based on the solid content of the active material suspension.

7. A coated catalyst for the catalytic gas-phase oxidation of aromatic hydrocarbons to a member selected from carboxylic acids and carboxylic anhydrides, consisting essentially of an essentially inert carrier core of quartz, porcelain, magnesium oxide, silicon carbide, tin oxide, rutile, alumina, aluminum silicate, magnesium silicate, zirconium silicate or cerium silicate or mixtures thereof and a layer of catalytically active metal oxides applied the carrier core in amounts from 5 to 20% by weight, based on the amount of the carrier, in shell form comprising as essential constituents titanium oxide of the anatase type and vanadium pentoxide as well as a binder consists essentially of
   A) a polymer obtained by free-radical polymerization, comprising 5 to 100% by weight of monomers (a) in the form of ethylenically unsaturated acid anhydrides or ethylenically unsaturated dicarboxylic acids whose carboxyl groups can form an anhydride and 0 to 95% by weight of further monoethylenically unsaturated monomers (b), with the proviso that the monomers (a) and (b) on average have at most 6 carbon atoms and
   B) an alkanolamine having at least 2 OH groups, at most 2 nitrogen atoms and at most 6 C atoms and wherein the content of the binder, based on the amount of the active metal oxides, is 1 to 10% by weight.

8. A process for the catalytic gas-phase oxidation of aromatic hydrocarbons to carboxylic acids and optionally carboxylic anhydrides which comprises contacting the aromatic hydrocarbons with molecular oxygen in a fixed bed reactor at elevated temperature in the presence of one or more coated catalysts as defined in claim 7 arranged in the reactor in layers.

9. A process for catalytically oxidizing xylene and/or naphthalene to phthalic anhydride which comprises contacting xylene and/or naphthalene with molecular oxygen, at elevated temperatures in a fixed bed containing the catalyst of claim 7.

* * * * *

UNITED STATES PATENT AND TRADEMARK OFFICE
CERTIFICATE OF CORRECTION

PATENT NO.     : 6,528,683 B1
DATED          : March 4, 2003
INVENTOR(S)    : Heidemann et al.

It is certified that error appears in the above-identified patent and that said Letters Patent is hereby corrected as shown below:

<u>Title page,</u>
Item [22], PCT Filed, "Jun. 9, 1999" should be -- Jun. 2, 1999 --.

Item [57], ABSTRACT,
Line 12, "a binding agent" should be -- of a binding agent --.

Signed and Sealed this

Twenty-fourth Day of June, 2003

JAMES E. ROGAN
*Director of the United States Patent and Trademark Office*